United States Patent [19]

Kogawa et al.

[11] Patent Number: 5,130,450
[45] Date of Patent: Jul. 14, 1992

[54] PLATINUM COMPLEXES

[75] Inventors: Osamu Kogawa, Kashiwa; Kenji Iwata, Kuki; Hisao Ekimoto, Tokyo; Tadashi Ishii, Tokyo; Kimihiko Takada, Tokyo, all of Japan

[73] Assignee: Nippon Kayaku Kabushiki Kaisha, Tokyo, Japan

[21] Appl. No.: 688,903

[22] Filed: Apr. 19, 1991

[30] Foreign Application Priority Data

Apr. 25, 1990 [JP] Japan .................. 2-107341

[51] Int. Cl.$^5$ .............................. C07F 15/00
[52] U.S. Cl. ..................... 556/137; 556/136
[58] Field of Search ............... 556/136, 137; 514/492

[56] References Cited

U.S. PATENT DOCUMENTS

| | | | |
|---|---|---|---|
| 4,271,085 | 6/1981 | Amundsen et al. | 260/429 R |
| 4,482,569 | 11/1984 | Bulten et al. | 556/137 |
| 4,505,928 | 3/1985 | Amundsen et al. | 514/492 |
| 4,710,577 | 12/1987 | Kidani et al. | 556/137 |
| 4,748,254 | 5/1988 | Cheltsov-Bebutov et al. | 556/137 X |
| 4,760,157 | 7/1988 | Child et al. | 556/137 |
| 4,968,826 | 11/1990 | Totani et al. | 556/137 |

FOREIGN PATENT DOCUMENTS 36156 1/1991 Japan.

OTHER PUBLICATIONS

The Journal of Clinical Hematology and Oncology, vol. 7, No. 3, 1977, pp. 856-857.

*Primary Examiner*—Arthur C. Prescott
*Attorney, Agent, or Firm*—Nields & Lemack

[57] ABSTRACT

A platinum (II) complex represented by the general formula:

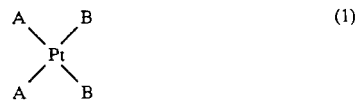

(1)

[wherein A's are each ammonia or two A's jointly represent 1,2-diaminocyclohexane, 1-amino-1-aminomethylcyclohexane or 1,4-diamino-2-methylbutane; and B's may be same or different and represent

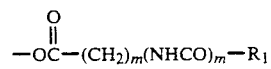

(wherein m is 0, 1 or 2; n is 0 or 1; $R_1$ is a $C_3$–$C_6$ alkyl group substituted with one or two hydroxyl groups) or two B's jointly represent

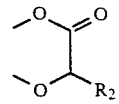

(wherein $R_2$ is a $C_2$–$C_5$ alkyl group substituted with one hydroxyl group)].

These platinum (II) complexes have high potencies for use as an antitumor agent.

12 Claims, No Drawings

PLATINUM COMPLEXES

BACKGROUND OF THE INVENTION

1. Field of the Invention

This invention relates to novel platinum complexes which have high potencies for use as an antitumor agent.

2. Statement of the Prior Art

It is already known that certain platinum complexes have an antitumor effect. For instance, cis-dichlorodiammine platinum (II) (general name: cis-Platin) has a very excellent antitumor effect and is widely used clinically at present (see, for instance, Journal of Phamaceutical Science, Vol. 65, No. 3, pp. 315–328, 1976, and Inorganic Biochemistry, Vol. 11, pp. 139–149, 1979). However, cis-Platin has strong side effects such as renal toxicity and vomitting toxicity and has also low solubility in water, which merely allows supply of liquid preparations of a low concentration. These problems have been the obstacles to the wider application of this compound in clinical therapeutics.

Recently, some new platinum complexes such as cis-1,1-cyclobutane dicarboxylato-diammine platinum [Japanese Patent Application Kokai (Laid-Open) No. 49-48621] and cis-O,O'-glycolato-diammine platinum [Japanese Patent Application Kokai(Laid-Open) No. 59-222497] have been developed.

These newly developed compounds, however, are disappointedly low in antitumor activity in comparison with cis-Platin. Therefore, a request has been voiced in the art for the obtainment of a platinum complex which has a strong antitumor activity, few side effects and high solubility in water.

SUMMARY OF THE INVENTION

As a result of extensive researches, the present inventors succeeded in synthesizing various platinum (II) complexes and found that these complexes have a higher antitumor activity than cis-Platin and are also readily soluble in water.

The present invention has been completed on the basis of the above finding.

The present invention relates to the platinum (II) complexes represented by the the general formula (1):

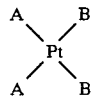

wherein two A's are each ammonia or jointly represent 1,2-diaminocyclohexane, 1-amino-1-aminomethylcyclohexane or 1,4-diamino-2-methylbutane; and each of B's represents

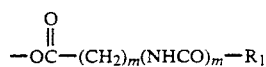

(wherein m is 0, 1 or 2; n is 0 or 1; $R_1$ is a $C_3$–$C_6$ alkyl group substituted with one or two hydroxyl groups) or two B's jointly form a group represened by

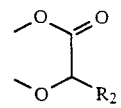

(wherein $R_2$ is a $C_2$–$C_5$ alkyl group substituted with one hydroxyl group).

DETAILED DESCRIPTION OF THE INVENTION

In the compounds of the present invention, the groups represented by $R_1$ in their formulae include, for example, $C_3$–$C_6$ alkyl groups substituted with one or two hydroxyl groups, such as hydroxypropyl, hydroxyisopropyl, hydroxybutyl, hydroxyisobutyl, hydroxysecbutyl, hydroxy-t-butyl, hydroxypentyl, hydroxy-1,1-dimethylpropyl, hydroxy-1-methylbutyl, hydroxyhexyl, dihydroxypropyl, dihydroxyisopropyl, dihydroxybutyl, dihydroxyisobutyl, dihydroxy-sec-butyl, dihydroxy-t-butyl, dihydroxypentyl, dihydroxy-1,1-dimethylpropyl, dihydroxy-1-methylbutyl, dihydroxyhexyl, etc., and cyclic hydroxypolymethylene groups such as hydroxytrimethylene, hydroxytetramethylene, hydroxypentamethylene, hydroxyhexamethylene, etc. In the process of this invention, $R_1$ preferably represents branched $C_3$–$C_5$ alkyl groups substituted with one or two hydroxy groups such as hydroxyisopropyl, hydroxy-t-butyl, hydroxy-1,1-dimethylpropyl, dihydroxy-1,1-dimethylpropyl, dihydroxy-1-methylbutyl and the like.

Regarding $R_2$ in the formulae of the compounds of this invention, the $C_2$–$C_5$ alkyl groups substituted with one hydroxyl group, which are represented by $R_2$, include hydroxypropyl, hydroxyisopropyl, hydroxybutyl, hydroxyisobutyl, hydroxy-t-butyl, hydroxypentyl, hydroxy-1,1-dimethylpropyl, hydroxy-1-methylbutyl and the like. The branched $C_3$–$C_5$ alkyl groups substituted with one hydroxyl group are preferred. A typical example of such groups is hydroxy-t-butyl.

Typical examples of the compounds represented by the general formula (1) are listed below. The compounds of this invention are not limited to these examples.

1. cis-bis(2,4-dihydroxy-3,3-dimethylbutyrato)-diammine platinum (II)
2. cis-bis(2-hydroxy-3,3-dimethylbutyrato)-diammine platinum (II)
3. cis-bis(1-hydroxy-cyclobutane-1-carboxylato)-diammine platinum (II)
4. cis-bis(2,4-dihydroxy-3,3-dimethylbutyrato)-1-amino-1-aminomethylcyclohexane platinum (II)
5. cis-bis(2,4-dihydroxy-3,3-dimethylbutyrato)-trans-1,2-diaminocyclohexane platinum (II)
6. cis-bis(2-hydroxy-3,3-dimethylbutyrato)-trans-1,2-diaminocyclohexane platinum (II)
7. cis-bis(1-hydroxy-cyclobutanecaroxylato)-trans-1,2-diammine platinum (II)
8. cis-bis(2-hydroxy-2-methylpropionato)-trans-1,2-diaminocyclohexane platinum (II)
9. cis-bis(3-hydroxy-2,2-dimethylpropionato)-trans-1,2-diaminocylohexane platinum (II)
10. cis-bis(3-hydroxy-2,2-dimethylpropionato)-diammine platinum (II)
11. cis-bis(3,5-dihydroxy-3-methylvalerato)-diammine platinum (II)

12. cis-bis(3,5-dihydroxy-3-methylvalerato)-trans-1,2-diaminocyclohexane platinum (II)
13. cis-bis(3-hydroxy-2,2-dimethylpropionato)-1-amino-1-aminomethylcyclohexane platinum (II)
14. cis-bis(3,5-dihydroxy-3-methylvalerato)-1-amino-1-aminomethylcyclohexane platinum (II)
15. cis-bis(pantothenato)-diammine platinum (II)
16. cis-bis(pantothenato)-trans-1,2-diaminocyclohexane platinum (II)
17. cis-[2-(2-hydroxy-1,1-dimethylethyl)-glycolato-O,O']-trans-1,2-diaminocyclohexane platinum (II)
18. cis-bis(2,4-dihydroxy-3,3-dimethylbutyrato)-1,4-diamino-2-methylbutane platinum (II)
19. cis-bis(3-hydroxy-2,2-dimethylpropionato)-1,4-diamino-2-methylbutane platinum (II)
20. cis-[2-(2-hydroxy-1,1-dimethylethyl)-glycolato-O,O']-1,4-diamino-2-methylbutane platinum (II)

The platinum complexes of the present invention can be produced by carrying out the following reactions.

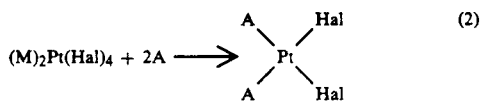

(wherein A is as defined above; M is an alkaline metal atom such as Na or K; and Hal is a halogen atom such as Cl, Br or I).

A halogenated primary platinum salt, preferably halogenated potassium primary platinate, and a diamine such as ammonia, 1,2-diaminocyclohexane, 1-amino-1-aminomethylcyclohexane, 1,4-diamino-2-methylbutane or the like are reacted in an aqueous solution to obtain a dihalogenodiamine platinum complex. The diamine is used in an amount of 0.5 to 2 moles, preferably 0.9 to 1.2 moles per 1 mole of the tetrahalogenoplatinate. The reaction is carried out at 0° to 100° C., preferably 20° to 50° C. with stirring.

Next, as shown in the following reaction scheme, the dihalogenodiamine platinum (2) is suspended in water and added with an aqueous silver nitrate solution and the resulting silver halide precipitate is removed by filtration to obtain an aqeuous solution of a diaquacomplex (3).

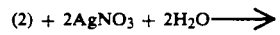

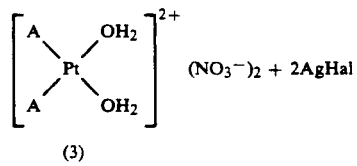

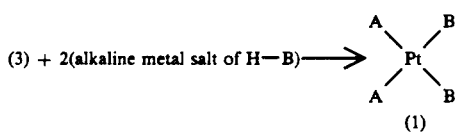

(wherein A and B are as defined above).

The water for suspending the dihalogenodiamine complex (2) can be used in an appropriate amount. The amount of silver nitrate is 2 moles or less, particularly preferably 1.9 to 2 moles to 1 mole of the dihalogenodiamine complex (2). The reaction is conducted at 0° to 100° C., preferably 20° to 80° C. with stirring.

Then, the diaquacomplex (3) is reacted with alkaline metal salt of the compound represented by the formula:

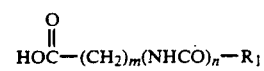

(wherein m is 0, 1 or 2; n is 0 or 1; $R_1$ is a $C_3$–$C_6$ alkyl group substituted with one or two hydroxyl groups) such as pantoic acid, 3-hydroxy-2,2-dimethylbutyric acid, mevalonic acid, 2-hydroxy-2-methylpropionic acid, pantothenic acid or the like. For example, the reaction is carried out by adding an aqueous solution containing an appropriate amount of the alkaline metal salt of said compound to the aqueous solution of the diaquacomplex (3). The alkaline metal salt of said compound is used in an amount of usually 2 to 6 moles per 1 mole of the diaquacomplex (3). The reaction can be conducted at 0° to 100° C., preferably at 20° to 70° C. to obtain compounds represented by the formula (1).

The obtained crude crystals are purified by silica gel column chromatography using a methanolchloroform mixed solvent or by recrystallization or reprecipitation with an acetone-methanol mixed solvent or the like.

Particularly, a compound of the following formula (4):

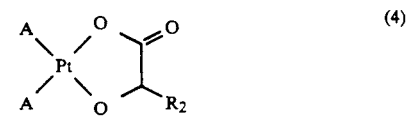

(wherein A and $R_2$ are as defined above) can be synthesized from the following reaction.

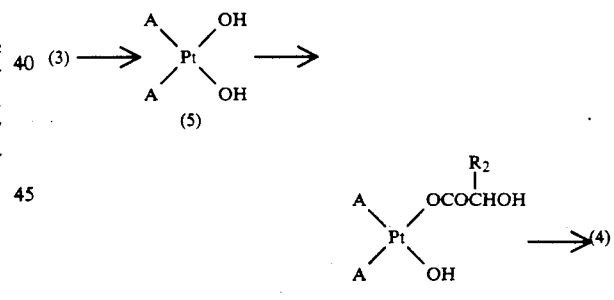

An aqueous solution of the diaquacomplex (3) is passed through a column packed with an anion exchange resin (OH type) to obtain a dihydroxydiamine platinum complex (5). This dihydroxydiamine platinum complex (5) is reacted with a 2-R2-glycolic acid (such as 2,4-dihydroxy-3,3-dimethylbutanoic acid) by adding the latter to an aqueous solution of said platinum complex (5) in an amount of 0.5 to 1.5 moles, preferably 0.7 to 1.0 mole per 1 mole of dihydroxydiamine platinum complex (5) to form a compound (6), from which the compound of the formula (4) can be obtained. The reaction (5)→(4) can be conducted at 0° to 90° C. and completed in several hours to 10 days, but the present reaction is a two-stage reaction involving the step of forming the compound (6), in which preferably the initial reaction is conducted at 10° to 40° C. for a period of several hours to several days and then heating is conducted at 40° to 70° C. for several hours to complete the reaction.

The process for the preparation of the compounds of this invention will be described below by way of examples.

EXAMPLE 1 cis-Bis[(R)-2,4-dihydroxy-3,3-dimethylbutyrato]diammine platinum (II) (compound No. 1)

390.5 mg of D-pantolactone was dissolved in 30 ml of a 0.1 N aqueous sodium hydroxide solution and reacted at room temperature for 3 hours to form an aqueous pantoic acid sodium salt solution. Separately, 321 mg of cis-dinitrato-diammine platinum (II) was dissolved in 50 ml of water, and thereto was added the previously prepared aqueous pantoic acid sodium salt solution. After 48-hour reaction at room temperature, water was evaporated away under reduced pressure. Methanol was added to the residue and the produced platinum complex was extracted. Then methanol was removed under reduced pressure to obtain a crude powdery product. This product was again dissolved in methanol and added with acetone, causing reprecipitation. The precipitate was filtered out and dried under reduced pressure to obtain 510 mg of the compound No. 1.

Melting point: 140°–144° C. (colored and decomposed)

Elementary analysis (calcd. for $C_{12}H_{28}N_2O_8Pt.1\frac{1}{2}H_2O$): Calculated (%): C, 26.18; H, 5.68; N, 5.09. Found (%): C, 25.40; H, 4.74; N, 5.92.

IR ($cm^{-1}$): 3420, 3260, 2960, 2875, 1630, 1480, 1350, 1045.

EXAMPLE 2 cis-Bis(2-hydroxy-3,3-dimethylbutyrato)-diammine platinum (II) (compound No. 2)

The reaction procedure of Example 1 was repeated except for using 193.7 mg of 2-hydroxy-3,3-dimethylbutyric acid and 235.5 mg of cis-dinitratodiammine platinum (II) to obtain 100 mg of the compound No. 2.

Melting point: 177°–182° C. (decomposed)

Elementary analysis (calcd. for $C_{12}H_{28}H_2O_6Pt.H_2O$): Calculated (%): C, 28.29; H, 5.94; N, 5.50. Found (%): C, 28.26; H, 6.06; N, 5.15.

IR ($cm^{-1}$): 3400, 3220, 2950, 2910, 2870, 1630, 1490, 1380, 1260, 1080, 1020, 765.

EXAMPLE 3 cis-Bis(1-hydroxy-cyclobutane-1-carboxylato)-diammine platinum (II) (compound No. 3)

The procedure of Example 1 was repeated except for use of 302 mg of cyclobutane-1-hydroxy-1-carboxylic acid and 353.1 mg of cis-dinitratodiammine platinum (II) to obtain 450 mg of the compound No. 3.

Melting point: 150°–155° C. (decomposed)

Elementary analysis (calcd. for $C_{12}H_{20}N_2O_6Pt$): Calculated (%): C, 26.15; H, 4.39; N, 6.10. Found (%): C, 26.42; H, 3.57; N, 6.85.

IR ($cm^{-1}$): 3420, 3270, 2990, 2940, 1620, 1590, 1370, 1255, 1165.

EXAMPLE 4 cis-Bis[(R)-2,4-dihydroxy-3,3-dimethylbutyrato]-1-amino-1-aminomethylcyclohexane platinum (II) (compound No. 4)

448 mg (1 mmol) of cis-dinitrato-(1-amino-1-aminomethylcyclohexane) platinum (II) was dissolved in 40 ml of water. Thereto was added a solution prepred by dissolving 262 mg (2 mmol) of D-pantolactone in 5 ml of water, adding thereto 1.0 ml of 2N sodium hydroxide, leaving the mixed solution as it was for a while and adjusting the solution pH to about 7. The resulting solution was allowed to stand at room temperature for 2 days. It was then evaporated to dryness under reduced pressure and put into a chloroform/methanol (4:1) mixed solvent, followed by stirring. The resulting solution was filtered to remove the insolubles. Then the solvents in the filtrate were distilled away and the residue was purified by silica gel chromatography to obtain 400 mg of the compound No. 4 in a yield of 65%.

Melting point: 150°–153° C. (colored and decomposed)

Elementary analysis (calcd. for $C_{19}H_{36}N_2O_8Pt.1\frac{1}{2}H_2O$): Calculated (%): C, 35.43; H, 6.30; N, 4.27. Found (%): C, 35.40; H, 6.41; N, 4.35.

IR ($cm^{-1}$): 3425, 3230, 2950, 2880, 1640, 1470, 1350, 1130, 1080, 1050, 770.

EXAMPLE 5 cis-Bis[(R)-2,4-dihydroxy-3,3-dimethylbutyrato]-trans-(R,R)-1,2-diaminocyclohexane platinum (II) (compound No. 5)

The procedure of Example 1 was repeated by using 433 mg of cis-dinitrato-[trans-(R,R)-1,2-diaminocyclohexane] platinum (II) to obtain 360 mg of the compound No. 5 (yield: 60%).

Melting point: 150°–155° C. (colored and decomposed)

Elementary analysis (calcd. for $C_{18}H_{36}N_2O_8pt.1\frac{1}{2}H_2O$): Calculated (%): C, 34.05: H, 6.07: N, 4.20. Found (%): C, 34.28: H, 6.23: N, 4.44.

IR ($cm^{-1}$): 3400, 3230, 2940, 2875, 1630, 1480, 1350, 1265, 1180, 1070, 1055, 760.

EXAMPLE 6 cis-Bis(2-hydroxy-3,3-dimethylbutyrato)trans-1,2-diaminocyclohexane platinum (II) (compound No. 6)

158.4 mg of 2-hydroxy-3,3-dimethylbutyric acid was dissolved in 6 ml of a 0.2 N aqueous solution of sodium hydroxide. Separately, 190.1 mg of cis-dichloro-trans-1,2-diaminocyclohexane platinum (II) was suspended in 5 ml of water. To this suspension was added a solution of 168.2 mg of silver nitrate in 5 ml of water, and the mixed solution was stirred at room temperature for 2 hours, further reacted at 70° C. for one hour, then cooled down to 10° C. and filtered. The resulting dinitrato-aquacomplex solution was added with the previously prepared sodium hydroxide solution of said carboxylic acid, and the mixed solution was stirred at room temperature for 12 hours, followed by evaporation of water under reduced pressure. The residue was subjected to the same purifying treatment as in Example 1 to obtain 250 mg of the compound No. 6.

Melting point: 210°–215° C. (decomposed)

Elementary analysis (calcd. for $C_{18}H_{36}N_2O_6Pt$): Calculated (%): C, 37.82; H, 6.35; N, 4,90. Found (%): C, 37.32; H, 5.96; N, 5.02.

IR ($cm^{-1}$): 3420, 3220, 2950, 2870, 1620, 1480, 1385, 1240, 1080, 1020, 760.

EXAMPLE 7 cis-Bis(1-hydroxy-cyclobutanecarboxylato)-trans-1,2-diammine platinum (II) (compound No. 7)

The reactions and the treatments in Example 6 were repeated by using 139.3 mg of cyclobutane-1-hydroxy-1-carboxylic acid and 190.1 mg of dichloro-trans-1,2-diaminocyclohexane platinum (II) to obtain 210 mg of the compound No. 7.

Melting point: 205°–210° C. (decomposed)

Elementary analysis (calcd. for $C_{16}H_{28}N_2O_6Pt$): Calculated (%): C, 35.62; H, 5.23; N, 5.19. Found (%): C, 35,58; H, 4.05; N, 5.71.

IR ($cm^{-1}$): 3420, 3220, 2940, 2860, 1620, 1450, 1395, 1255, 1170.

EXAMPLE 8 cis-Bis(2-hydroxy-2-methylpropionato)-trans-1,2-diaminocyclohexane platinum (II) (compound No. 8)

433 mg of cis-dinitrato-trans-1,2-diaminocyclohexane was dissolved in water and added with a solution (pH 7) composed of 229 mg of 2-hydroxy-2-methylpropionic acid, 5 ml of water and 1.1 ml of 2N sodium hydroxide, followed by stirring at 50°–55° C. for 3 hours. The reaction solution was filtered and then concentrated under reduced pressure. After cooling the concentrate with ice, the crystals were filtered out, washed with water and dried to obtain 330 mg of the compound No. 8 (yield: 64%).

Melting point: 219°–222° C. (decomposed)

IR ($cm^{-1}$): 3420, 3220, 2950, 2875, 1630, 1470, 1385, 1330, 1200, 1160, 980.

EXAMPLE 9 cis-Bis[(S)-2,4-dihydroxy-3,3-dimethylbutyrato]-trans-(R,R)-1,2-diaminocyclohexane platinum (II) (compound No. 9)

The reactions, treatments and purification were conducted in the same manner as in Example 4 by using 433 mg of cis-dinitrato-trans-(R,R)-1,2-diaminocyclohexane platinum (II) and 340 mg of (S)pantolactone to obtain 290 mg of the compound No. 9 (yield: 48%).

Melting point: 148°–156° C. (decomposed)

IR ($cm^{-1}$): 3430, 3225, 2950, 2880, 1630, 1460, 1350, 1190, 1075, 1050, 760.

EXAMPLE 10 cis-Bis(3-hydroxy-2,2-dimethylpropionato)-trans-1,2-diaminocyclohexane platinum (II) (compound No. 10)

The procedure of Example 8 was repeated except for use of 433 mg of cis-dinitrato-trans-1,2-diaminocyclohexane platinum (II) and 260 mg of 3-hydroxy-2,2-dimethylbutyric acid to obtain 460 mg of the compound No. 10 (yield: 85%).

Melting point: 217°–218° C. (decomposed)

IR ($cm^{-1}$): 3400, 3230, 2950, 2880, 1615, 1565, 1480, 1395, 1350, 1240, 1160, 1055, 1040.

EXAMPLE 11 cis-Bis(3-hydroxy-2,2-dimethylpropionato)-diammine platinum (II) (compound No. 11)

The procedure of Example 8 was repeated except for use of 353 mg of cis-dinitrato-diammine platinum (II) and 260 mg of 3-hydroxy-2,2-dimethylbutyric acid to obtain 350 mg of the compound No. 11 (yield: 38%).

Melting point: 178°–180° C. (decomposed)

IR ($cm^{-1}$): 3420, 3300, 2950, 2920, 1615, 1550, 1480, 1360, 1280, 1195, 1045.

EXAMPLE 12 cis-Bis(3,5-dihydroxy-3-methylvalerato)-diammine platinum (II) (compound No. 12)

The procedure of Example 1 was repeated except for use of 353 mg of cis-dinitrato-diammine platinum (II) and 260 mg of mevalonic lactone to obtain 355 mg of the compound No. 12 (yield: 68%).

Melting point: 123°–130° C. (decomposed)

IR ($cm^{-1}$): 3410, 3260, 2975, 2940, 1615, 1390, 1270, 1130, 1060, 1030.

EXAMPLE 13

Cis-Bis(3,5-dihydroxy-3-methylvalerato)-trans-1,2-diaminocyclohexane platinum (II) (compound No. 13)

The procedure of Example 4 was repeated except for use of 433 mg of cis-dinitrato-trans-1,2-diaminocyclohexane platinum (II) and 260 mg of mevalonic lactone to obtain 430 mg of the compound No. 13 (yield: 71%).

Melting point: 164°–167° C. (decomposed)

IR ($cm^{-1}$): 3400, 3250, 2970, 2870, 1640, 1620, 1460, 1395, 1260, 1160, 1020.

EXAMPLE 14 cis-Bis(3-hydroxy-2,2-dimethylpropionato)-1-amino-1-aminomethylcyclohexane platinum (II) (compound No. 14)

The procedure of Example 1 was repeated by using 448 mg of cis-dinitrato-1-amino-1-aminomethylcyclohexane platinum (II) and 260 mg of 3-hydroxy-2,2-dimethylpropionic acid. After the reaction, water was evaporated away under reduced pressure and the reaction mixture was extracted with ethanol. Then ethanol was evaporated away from the extract and the resulting product was purified by silica gel chromatography using a chloroform-methanol mixed solvent to obtain 470 mg of the compound No. 14 (yield: 84%).

Melting point: 196°–198° C. (decomposed)

IR ($cm^{-1}$): 3420, 3220, 2930, 2870, 1620, 1565, 1480, 1400, 1355, 1165, 1050.

EXAMPLE 15 cis-Bis(3,5-dihydroxy-3-methylvalerato)-1-amino-1-aminomethylcyclohexane platinum (II) (compound No. 15)

The procedure of Example 4 was repeated except for use of 335 mg of cis-dinitrato-1-amino-1-aminomethylcyclohexane platinum (II) and 195 mg of mevalonic lactone to obtain 490 mg of the compound No. 15 (yield: 81%).

Melting point: 120°–125° C. (decomposed)

IR ($cm^{-1}$): 3400, 3210, 2925, 2850, 1615, 1450, 1380, 1270, 1130, 1060, 1020.

EXAMPLE 16 cis-Bis[(R)-pantothenato]-diammine platinum (II) (compound No. 16)

The procedure of Example 14 was repeated by using 353 mg of cis-dinitrato-diammine platinum (II) and 485 mg of sodium R-pantothenate to obtain 500 mg of the compound No. 16 (yield: 75%).

Melting point: 120°–135° C. (decomposed)

IR (cm$^{-1}$): 3400, 3275, 2960, 2880, 1640, 1550, 1400, 1325, 1280, 1200, 1080, 1060.

EXAMPLE 17 cis-Bis[(R)-pantothenato]-trans-(R,R)-1,2-diaminocyclohexane platinum (II) (compound No. 17)

The procedure of Example 14 was repeated except for use of 433 mg of cis-dinitrato-trans-(R,R)-1,2-diaminocyclohexane platinum (II) and 485 mg of sodium R-pantothenate to obtain 590 mg of the compound No. 17 (yield: 79%).

Melting point: 110°–130° C. (decomposed)

IR (cm$^{-1}$): 3400, 3300, 2950, 2880, 1645, 1545, 1460, 1400, 1315, 1260, 1050.

EXAMPLE 18 cis-[2-(2-Hydroxy-1,1-dimethylethyl)-glycolato-O,O']-trans-1,2-diaminocyclohexane platinum (II) (compound No. 18)

650 mg of cis-dinitrato-trans-1,2-diaminocyclohexane platinum (II) was dissolved in 100 ml of water under heating, and the solution was concentrated to about 10 ml and passed through a column packed with an anion exchange resin Dowex 1-8X. Separately, a solution was prepared from 198 mg of R-pantolactone, 5 ml of water and 0.75 ml of 2N sodium hydroxide solution, and this solution was left at room temperature for one hour and then passed through a column packed with a cation exchange resin Dowex 50W-4X. Said both solutions were mixed and stirred first at room temperature for 20 hours and then at 60°–65° C. for 4 hours. The reaction solution was filtered, water was evaporated away under reduced pressure, the remaining filtrate was extracted with a chloroform-methanol (3:1) mixed solution, and then the solvents were distilled away. The resulting product was purified by silica gel chromatography using a chloroform-methanol (3:1) mixed solution as solvent to obtain 410 mg of the compound No. 18 (yield: 66%).

Melting point: 226°–228° C. (decomposed)

IR (cm$^{-1}$): 3410, 3210, 2950, 2880, 1640, 1470, 1330 1180, 1060, 1040.

EXAMPLE 19 cis-Bis[(R)-2,4-dihydroxy-3,3-dimethylbutyrato]-(R)-1,4-diamino-2-methylbutane platinum (II) (compound No. 19)

The procedure of Example 4 was repeated except for using 421 mg of cis-dinitrato-(R)-1,4-diamino-2-methylbutane and 262 mg of (R)-pantolactone to obtain 425 mg of the compound No. 19 (yield: 72%).

Melting point: 120°–130° C. (decomposed)

IR (cm$^{-1}$): 3430, 3250, 2980, 2900, 1640, 1470, 1350, 1090, 1060, 765.

EXAMPLE 20 cis-Bis(3-hydroxy-2,2-dimethylpropionato)(R)-1,4-diamino-2-methylbutane platinum (II) (compound No. 20)

The procedure of Example 14 was repeated except for use of 421 mg of cis-dinitrato-(R)-1,4-diamino-2-methylbutane platinum (II) and 248 mg of 3-hydroxy-2,2-dimethylpropionic acid to obtain 330 mg of the compound No. 20 (yield: 62%).

Melting point: 154°–160° C. (decomposed)

IR (cm$^{-1}$): 3400, 3225, 2960, 2925, 1620, 1480, 1410, 1360, 1260, 1170, 1050, 900.

EXAMPLE 21 cis-[2-(2-Hydroxy-1,1-dimethylethyl)-glycolato-O,O']-(R)-1,4-diamino-2-methylbutane platinum (II) (compound No. 21)

The procedure of Example 18 was repeated except for use of 834 mg of cis-dinitrato-(R)-1,4-diamino-2-methylbutane platinum (II) and 266 mg of DL-pantolactone to obtain 405 mg of the compound No. 21 (yield: 46%).

Melting point: 168°–173° C. (decomposed)

IR (cm$^{-1}$): 3420, 3220, 2950, 2875, 1635, 1460, 1340, 1055, 830, 755.

The solubility in water of the compounds of this invention is shown in Table 1.

TABLE 1

| Solubility in water (mg/ml) | Compound Nos. |
| --- | --- |
| >100 | 1, 4, 5, 9, 12, 13, 15, 16, 17, 18, 21 |
| >20 | 20 |
| >5 | 2, 3, 6, 7, 8, 10, 11, 14 |

In view of the fact that the solublity of cis-Platin in physiological saline solution is about 1.2 mg/ml, the compounds of this invention apparently have high solubility in water and are dissolved in water quickly. Therefore, in use of the compounds of this invention for intraarterial injection, they enable preparation of high-concentration formulations required for such injection. Also, the crystals of the compounds can be dissolved in water to an appropriate concentration and the prepared solutions can be immediately administered.

The antitumor effect of some representative examples of the compounds of this invention will be described below.

TEXT EXAMPLE 1

The PC-3 cells derived from lung cancer and the SW-1116 cells derived from colon cancer were prepared in the form of suspensions with cell populations of $1 \times 10^4$ cells/ml and $1.75 \times 10^4$ cells/ml, respectively, and each suspension was applied on a 96-well flat-bottomed microplate at a rate of 0.2 ml/well. After 24-hour incubation under the conditions of 37° C. and 5% $CO_2$, 10 μl of the novel fat-soluble platinum complex was added in various concentrations and the PC-3 cells and SW-1116 cells were further cultured for 72 hours and 96 hours, respectively. Thereafter, the culture was drawn off from each well by using an aspirator, fixed with MeOH, then added with a 0.05% methylene blue/10 mM tris-(hydroxymethyl)aminomethanehydrochloric acid buffer solution (pH 8.5) at a rate of 100 μl/well and stained at room temperature for 30 minutes. Thereafter, each well was cleared of the staining solution by using an aspirator and washed three times with pure water. Then 3% hydrochloric acid solution was added at a rate of 200 μl/well, and after sealing, the culture was left at room temperature for about 24 hours and the pigment was extracted from the cells. The absorbance ($A_{660}$) of each well at 660 nm was measured by a dynamic microplate reader, and the growth inhibition rate (%) at each concentration was calculated from the following equation. The inhibition rate was plotted on a logarithmic probability paper to determine the 50% inhibition concentration ($IC_{50}$).

$$\text{Growth inhibition rate (\%)} = \left(1 - \frac{A_{660} \text{ (in compound-treated group)}}{A_{660} \text{ (in control group)}}\right)$$

The results are shown in Table 2.

TABLE 2

| Compound No. | $IC_{50}$ (µg/ml) | |
| --- | --- | --- |
| | PC-3 | SW-1116 |
| 4 | 0.73 | 0.37 |
| 5 | 0.60 | 0.060 |
| 8 | 1.57 | 0.21 |
| 9 | 0.45 | 0.057 |
| 10 | 0.50 | 0.065 |
| 13 | 0.76 | 0.085 |
| 15 | 0.80 | 0.14 |
| 17 | 0.60 | 0.082 |
| 18 | 2.03 | 0.25 |
| 19 | 0.40 | 0.36 |
| 20 | 0.35 | 0.36 |
| 21 | 0.53 | 0.37 |
| cis-Platin | 0.40 | 0.36 |

As is appreciated from the foregoing results, the compounds of this invention have a strong cell growth inhibitory activity and are also highly soluble in water, so that these compounds have high potencies for use as a novel carcinostatic agent.

What is claimed is:

1. A platinum (II) complex represented by the general formula (1):

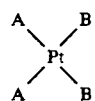

[wherein A's are each ammonia or two A's jointly represent 1,2-diaminocyclohexane, 1-amino-1-aminomethylcyclohexane or 1,4-diamino-2-methylbutane; and B's may be same or different and represents

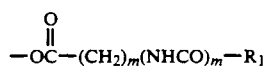

(wherein m is 0, 1 or 2; n is 0 or 1; $R_1$ is a $C_3$–$C_6$ alkyl group substituted with one or two hydroxyl groups) or two B's jointly represent

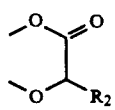

(wherein $R_2$ is a $C_2$–$C_5$ alkyl group substituted with one hydroxyl group)].

2. A platinum (II) complex according to claim 1, wherein in the formula (1), A's are each ammonia, and B's represent independently

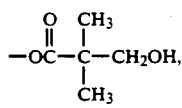

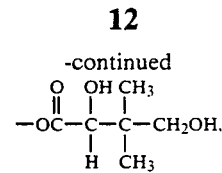

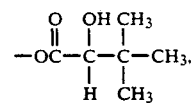

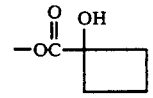

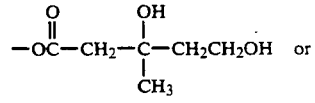

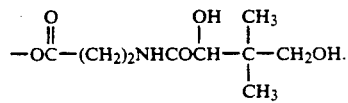

3. A platinum (II) complex according to claim 1, wherein two A's in the formula (1) are combined to represent 1,2-diaminocyclohexane.

4. A platinum (II) complex according to claim 1, wherein in the formula (1) B's represent independently

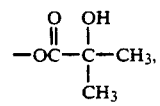

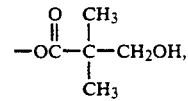

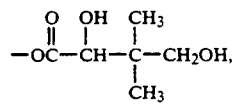

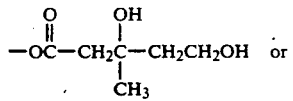

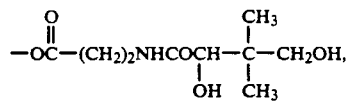

or two B's jointly represent 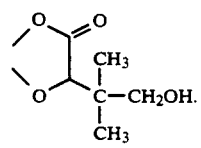

5. A platinum (II) complex according to claim 1, wherein in the formula (1), two A's jointly represent 1,2-diaminocyclohexane, and B's represent independently

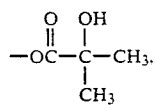

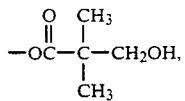

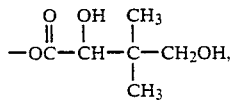

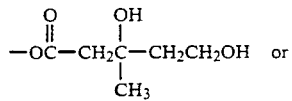 or

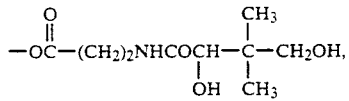

or two B's jointly represent 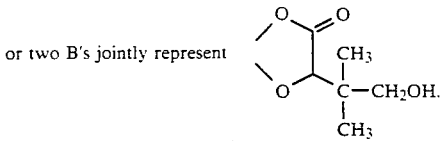

6. [cis-Bis(2,4-dihydroxy-3,3-dimethylbutyrato)-trans-1,2-diaminohexane]cis-Bis(2,4-dihydroxy-3,3-dimethylbutyrato)-trans-1,2-diaminocyclohexane platinum (II).

7. cis-Bis(3-hydroxy-2,2-dimethylpropionato)-trans-1,2-diaminocyclohexane platinum (II).

8. cis-Bis(3,5-dihydroxy-3-methylvalerato)-trans-1,2-diaminocyclohexane platinum (II).

9. cis-Bis(pantothenate)-trans-1,2-diaminocyclohexane platinum (II).

10. A medicinal composition comprising any of the compounds set forth in any one of claim 1 to 9 and a pharmaceutically acceptable carrier or diluent.

11. Any of the compounds set forth in any one of claims 1 or 9, which is used for the treatment of tumor in man or animals.

12. Use of any of the compounds set forth in any of claims 1 or 9 for preparing an antitumor agent.

* * * * *